US012220495B2

(12) United States Patent
Phungula et al.

(10) Patent No.: US 12,220,495 B2
(45) Date of Patent: Feb. 11, 2025

(54) MECHANICAL MULTI-STAGE CONNECTION AND DISCONNECTION MAINTAINING STERILE BARRIER

(71) Applicant: Medivators Inc., Minneapolis, MN (US)

(72) Inventors: Lindani Phungula, Southend On Sea (GB); Colin Oxford, Canvey Island (GB); Gary Spencer, Rayleigh (GB)

(73) Assignee: Medivators Inc., Minneapolis, MN (US)

( * ) Notice: Subject to any disclaimer, the term of this patent is extended or adjusted under 35 U.S.C. 154(b) by 697 days.

(21) Appl. No.: 17/440,231

(22) PCT Filed: Feb. 28, 2020

(86) PCT No.: PCT/US2020/020263
§ 371 (c)(1),
(2) Date: Sep. 17, 2021

(87) PCT Pub. No.: WO2020/190476
PCT Pub. Date: Sep. 24, 2020

(65) Prior Publication Data
US 2022/0175993 A1    Jun. 9, 2022

Related U.S. Application Data

(60) Provisional application No. 62/820,646, filed on Mar. 19, 2019.

(51) Int. Cl.
*A61L 2/00* (2006.01)
*A61L 2/18* (2006.01)
*A61L 2/22* (2006.01)

(52) U.S. Cl.
CPC ............... *A61L 2/186* (2013.01); *A61L 2/22* (2013.01); *A61L 2202/122* (2013.01);
(Continued)

(58) Field of Classification Search
CPC ... A61L 2/18; A61L 2/186; A61L 2/20; A61L 2202/24
(Continued)

(56) References Cited

U.S. PATENT DOCUMENTS 4,232,695 A   11/1980   Roberge
4,703,774 A   11/1987   Seehausen
(Continued)

FOREIGN PATENT DOCUMENTS

WO    WO2018/085506    5/2018

OTHER PUBLICATIONS

International Preliminary Report on Patentability issued in PCT/US2020/020263, mailed Sep. 30, 2021.
(Continued)

*Primary Examiner* — Monzer R Chorbaji

(57) ABSTRACT

A multistage connector assembly for a lumen decontamination system is provided. The assembly includes a main body, a multistage body, a multistage barrier, a connector, and one or more biasing members. The assembly includes a multistage barrier movable in the fluid passageway between a fully closed position in which each stage of the multistage barrier is in a closed position to each independently block flow in the fluid passageway and a fully open position in which each stage is in an open position to allow flow within the fluid passageway. The connector is configured to engage the multistage barrier when coupled to the main body to sequentially open each stage of the multistage barrier to enable flow through the fluid passageway. The biasing member(s) are configured to urge each stage of the multistage barrier towards a closed position that blocks flow in the fluid passageway.

20 Claims, 2 Drawing Sheets

(52) U.S. Cl.
CPC ..... *A61L 2202/123* (2013.01); *A61L 2202/14* (2013.01); *A61L 2202/18* (2013.01); *A61L 2202/24* (2013.01)

(58) Field of Classification Search
USPC ............ 422/28, 33, 292, 560, 295, 297, 300
See application file for complete search history.

(56) References Cited

U.S. PATENT DOCUMENTS

| | | |
|---|---|---|
| 7,294,305 B2 | 11/2007 | Lin et al. |
| 2005/0191208 A1* | 9/2005 | Lin .......................... A61L 2/16 422/33 |

OTHER PUBLICATIONS

International Search Report and Written Opinion of the International Searching Authority Dated May 15, 2020, of International PCT Application No. PCT/US2020/020263 filed Feb. 28, 2020.
Pressure Regulator (Wikipedia); available on Feb. 7, 2017; figure 3, p. 2; < https://en.wikipedia.org/wiki/Pressure_regulator >; accessed on Oct. 4, 2021.

* cited by examiner

MECHANICAL MULTI-STAGE CONNECTION AND DISCONNECTION MAINTAINING STERILE BARRIER

PRIORITY CLAIM

This application claims priority to and the benefit of U.S. Provisional application with Ser. No. 62/820,646, filed on Mar. 19, 2019, entitled MECHANICAL MULTI-STAGE CONNECTION AND DISCONNECTION MAINTAINING STERILE BARRIER, which is herein incorporated by reference in its entirety.

TECHNICAL FIELD

This disclosure relates generally to decontamination of medical devices; in particular, this disclosure relates to a multi-stage connector assembly that is able to maintain a sterile barrier.

BACKGROUND

Robust medical instruments are often sterilized at high temperatures. Commonly, the instruments are sterilized in a steam autoclave under a combination of high temperature and pressure. While such sterilization methods are very effective for more durable medical instruments, advanced medical instruments formed of rubber and plastic components with adhesives are delicate and wholly unsuited to the high temperatures and pressures associated with a conventional steam autoclave. Steam autoclaves have also been modified to operate under low pressure cycling programs to increase the rate of steam penetration into the medical devices or associated packages of medical devices undergoing sterilization. Steam sterilization using gravity, high pressure or pre-vacuum create an environment where rapid changes in temperature can take place. In particular, highly complex instruments which are often formed and assembled with very precise dimensions, close assembly tolerances, and sensitive optical components, such as endoscopes, may be destroyed or have their useful lives severely curtailed by harsh sterilization methods employing high temperatures and high or low pressures.

Endoscopes can also present problems in that such devices typically have numerous exterior crevices and interior lumens which can harbor microbes. Microbes can be found on surfaces in such crevices and interior lumens as well as on exterior surfaces of the endoscope. Other medical or dental instruments which comprise lumens, crevices, and the like can also provide challenges for decontaminating various internal and external surfaces that can harbor microbes.

The terminal package in which the lumen device resides during decontamination must maintain a sterile barrier. This prevents microbes or other contaminants from entering the terminal package after the lumen device has been decontaminated until the lumen device is ready to be used by a health care provider. To maintain the sterile barrier, existing terminal packages use a membrane that allows sterilant fluid to pass through, but prevents contaminants from entering the terminal package. However, these membranes can greatly reduce flow through the terminal package, which tends to create a pressure drop.

Therefore, a need exists that overcomes one or more of the disadvantages of present decontamination systems.

SUMMARY OF THE INVENTION

According to one aspect, this disclosure provides a decontamination system for a lumen device. The decontamination system comprises a decontamination chamber, a terminal package, and a connector assembly. The decontamination chamber defines a lumen device receiving area. The terminal package is dimensioned to be received within the lumen device receiving area and is configured to establish a sterile barrier for an interior of the terminal package. The connector assembly is operably associated with the terminal package. The connector assembly comprises a main body, a multistage barrier, a connector, and one or more biasing members. The main body defines a fluid passageway to establish fluid communication with the interior of the terminal package. The multistage barrier is movable in the fluid passageway between a fully closed position in which each stage of the multistage barrier is in a closed position in which each stage independently blocks flow in the fluid passageway and a fully open position in which each stage is in an open position to allow flow within the fluid passageway. The connector is configured to be coupled with the main body such that the connector engages the multistage barrier when coupled to the main body to sequentially open each stage of the multistage barrier to enable fluid communication between the connector and the interior of the terminal package. The biasing member(s) are configured to urge each stage of the multistage barrier towards a closed position that blocks flow in the fluid passageway.

According to another aspect, this disclosure provides a multistage connector assembly with a main body, a multistage body, a multistage barrier, a connector, and one or more biasing members. The main body defines a fluid passageway therethrough. The assembly includes a multistage barrier movable in the fluid passageway between a fully closed position in which each stage of the multistage barrier is in a closed position to each independently block flow in the fluid passageway and a fully open position in which each stage is in an open position to allow flow within the fluid passageway. The connector is configured to be coupled with the main body. The connector is configured to engage the multistage barrier when coupled to the main body to sequentially open each stage of the multistage barrier to enable flow through the fluid passageway. The one or more biasing members are configured to urge each stage of the multistage barrier towards a closed position that blocks flow in the fluid passageway.

BRIEF DESCRIPTION OF THE DRAWINGS

The present disclosure will be described hereafter with reference to the attached drawings which are given as non-limiting examples only, in which.

Figure 1:
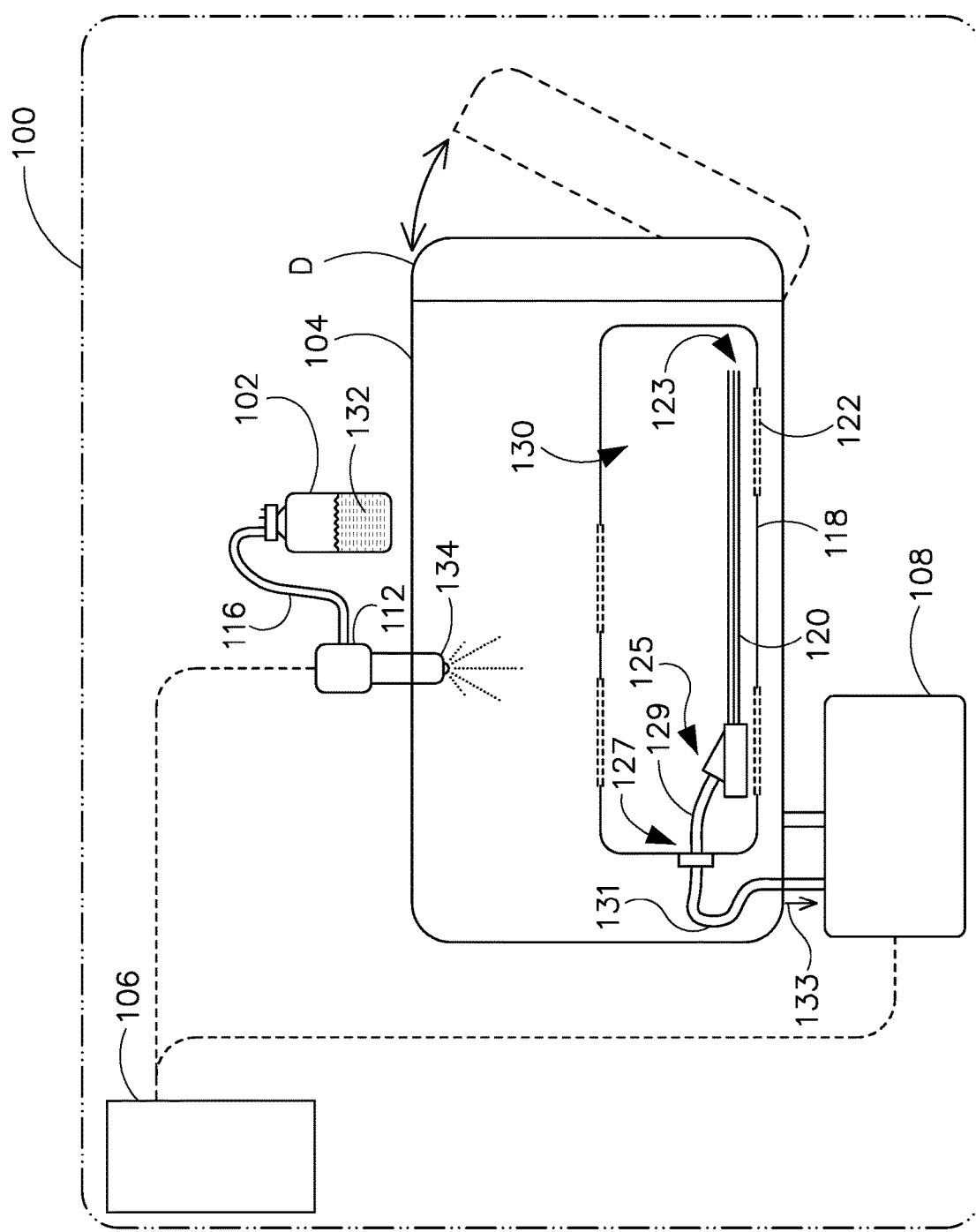
FIG. 1 is diagrammatic view of a decontamination system according to an embodiment of the present disclosure.

Corresponding reference characters indicate corresponding parts throughout the several views. The components in the figures are not necessarily to scale, emphasis instead being placed upon illustrating the principals of the invention. The exemplification set out herein illustrates embodiments of the invention, and such exemplification is not to be construed as limiting the scope of the invention in any manner.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the disclosure.

This disclosure relates to a multistage connector assembly for a decontamination system, such as to decontaminate a lumen device. In some embodiments, the multistage connector assembly is operably associated with the terminal package of the decontamination system. When the connector assembly is connected during a decontamination process, there is no membrane barrier interrupting flow. Instead of maintaining the sterile barrier of the terminal package with a membrane, which limits flow, the connector assembly mechanically maintains the terminal package's sterile barrier after disconnection (i.e., post-decontamination process). In this manner, the multistage connector assembly can dramatically increase the flow rate during decontamination because the flow is uninterrupted by a membrane barrier while mechanically maintaining the terminal package's sterile barrier post-decontamination. Although the multistage connector assembly is described herein with regard to a terminal package, embodiments are contemplated in which the multistage connector assembly could be integrated into other devices that maintain a sterile barrier. For example, the multistage connector assembly could be installed in-line in a tube or other fluid conduit instead of integrated into the terminal package.

FIG. 1 is a diagrammatic view of one embodiment of a system 100 for decontaminating a medical, dental, or other device having one or more lumens extending therethrough. As shown, the system 100 includes a reservoir 102, a decontamination chamber 104, a system controller 106, an environmental monitoring and control system 108, and vaporizer 112 which is connected to the reservoir 102 by conduit 116. A terminal package 118 containing a lumen device 120 for decontamination may be placed within the decontamination chamber 104. In the illustrated embodiment, the terminal package 118 can include a plurality of openings or pores 122. The reservoir 102 may be in fluid communication with the decontamination chamber 104 via vaporizer 112 to spray sterilant fluid into the terminal package 118. As shown, the sterilant fluid enters the terminal package 118 through pores 122 and enters lumen device 120 through a distal end 123. The sterilant fluid exits out the proximal end 125 of the lumen device 125. In the embodiment shown, the proximal end 125 is fluidly connected to a multistage connector assembly 127 via a fluid connector 129, which is in turn fluidly connected to the environmental monitoring and control system 108 via a fluid connector 131. The environmental monitoring and control system 108 may be configured to draw the sterilant fluid out of the proximal end 125 of the lumen device 120 as shown by arrow 133. Although this embodiment shows a single fluid connector 129, the multistage connector assembly 127 could be configured as a multi-connection for all channels of the lumen device 120 depending on the circumstances.

The system controller 106 provides control signals to and/or receives condition sensing and equipment status signals from the reservoir 102, the decontamination chamber 104, environmental monitoring and control system 108 and the vaporizer 112. In some embodiments, the system 100 can be assembled in a device small enough to sit on a tabletop or counter. For example, the decontamination chamber 104 may have an interior volume of less than about ten cubic feet.

The lumen device 120 to be decontaminated can be placed into the decontamination chamber 104 by opening the door D and placing the lumen device 120 on a rack or other supporting assembly in the interior of the decontamination chamber 104. In some embodiments, the lumen device 120 may be enclosed in the terminal package 118 before being placed in the decontamination chamber 104. In the example shown, the terminal package 118 defines a lumen device receiving area 130 to receive the lumen device 120 for decontamination.

The reservoir 102 may be a holding tank or other assembly configured to hold a sterilant fluid 132. In some embodiments, the sterilant fluid 132 can be a chemical or other substance suitable for use in a sterilization process that complies with the International Organization for Standardization (ISO) standard ISO/TC 198, Sterilization of Healthcare Products and/or the Association for the Advancement of Medical Instrumentation (AAMI) standard ANSI/AAMI/ISO 11140-1:2005, "Sterilization of Healthcare Products—Chemical Indicators—Part I: General Requirements" (Arlington, Va.: AAMI 2005). In some embodiments, the sterilant fluid 132 can be a room temperature (e.g., 20° C. to 25° C.) substance that can be dispersed as a fluid, such as a liquid, a vapor, or a combination thereof (such as a fog) during the decontamination process. Suitable substances for the sterilant fluid 132 include hydrogen peroxide ($H_2O_2$) and peracetic acid (PAA).

In various embodiments, the sterilant fluid is a composition that includes: (a) hydrogen peroxide; (b) organic acid; (c) a polymeric sulfonic acid resin based chelator; and (d) surfactant. The composition includes less than about 1 wt. % of an anticorrosive agent. The composition can further optionally include water.

In one aspect, the hydrogen peroxide present in the composition can be from about 0.5 wt. % to about 30 wt. %, from about 0.5 wt. % to about 1.5 wt. %, from about 0.8 wt. % to about 1.2 wt. %, from about 20 wt. % to about 30 wt. % and all ranges and values from about 0.5 wt. % to about 30 wt. %.

In another aspect, the acetic acid present in the composition can be from about 1 wt. % to about 25 wt. %, from about 4 wt. % to about 20 wt. %, from about 4.5 wt. % to about 5.5 wt. %, from about 9 wt. % to about 17 wt. % and all ranges and values from about 1 wt. % to about 25 wt. %.

In still another aspect, the peracetic acid present in the composition can be from about 0.01 wt. % to about 25 wt. %, from about 0.05 wt. % to about 20 wt. %, from about 0.05 wt. % to about 0.1 wt. %, from about 3.5 wt. % to about 8 wt. % and all ranges and values from about 0.01 wt. % to about 25 wt. %.

In yet another aspect, the polymeric resin chelator present in the composition can be from about 0.1 wt. % to about 5 wt. %, from about 0.2 wt. % to about 2 wt. %, from about 0.5 wt. % to about 1.5 wt. % and all ranges and value from about 0.1 wt. % to about 5 wt. %.

In various embodiments, the present invention provides for a composition that includes: (a) hydrogen peroxide, present in a concentration of about 0.5 wt. % to about 30 wt. %, e.g., about 28 wt. %; (b) acetic acid, present in a concentration of about 3 wt. % to about 25 wt. %, e.g., about 16 wt. %; (c) a sulfonic acid supported polymeric resin chelator present in a concentration of about 0.1 wt. % to about 5 wt. %, e.g., about 0.2 wt. % to about 0.7 wt. %; and, optionally, (d) Pluronic® 10R5 surfactant block copolymer, present in a concentration of about 2.0 wt. %, wherein the composition comprises less than about 0.1 wt. % of an anticorrosive agent, e.g., 0 wt. % of an anticorrosive agent. The composition can further optionally include water. In some embodiments, the hydrogen peroxide and acetic acid can combine to form peracetic acid, present in about 4 wt. % to about 8 wt. %, e.g., 6.8-7.5 wt. %.

In certain aspects, the peracetic acid/hydrogen peroxide compositions are stabilized without the need for a phosphonic based chelator, such as 1-hydroxyethylidene-1,1,-diphosphonic acid. In other aspects, a phosphonic based chelator, such as 1-hydroxyethylidene-1,1,-diphosphonic acid can be included in the sterilant fluid and therefore, component c), the polymeric sulfonic acid resin is optional.

The use of the polymeric stabilizer is detailed in U.S. application 62/737,453, filed Sep. 27, 2018, entitled "Peracetic Acid Stabilized Compositions with Polymeric Resins Chelators", the contents of which are incorporated herein by reference.

The terminal package 118 is sized so that the lumen device 120 to be decontaminated fits within the terminal package 118. In some embodiments, the terminal package 118 may be generally described as having a top, a bottom, and four sides extending between the top and bottom to create a cube-like structure. However, the terminal package 118 may have any suitable shape which encloses the lumen device 120. In some embodiments, the terminal package 118 may be formed from a rigid material such that the terminal package 118 has a rigid or structured shape. Alternatively, the terminal package 118 may be formed from a flexible material such that the terminal package 118 has a flexible shape. Suitable materials for the terminal package 118 include but are not limited to a polymeric non-woven sheet, such as spun-bonded polyethylene (e.g., Tyvek®, sold by E.I. du Pont de Nemours and Company, Wilmington, Del.), and polymeric materials such as polyester and polypropylene. Suitable materials for the terminal package 118 having a rigid or structured shape include but are not limited to various metals such as aluminum, stainless steel and/or various polymers in rigid form such as polyethylene and/or polypropylene.

The lumen device 120 may be positioned within the terminal package 118 and subjected to one or more decontamination cycles. Suitable lumen devices include any medical, dental or other device having at least one lumen extending through at least a portion of the device. In some embodiments, the lumen device 120 may include at least one lumen extending the entire length of the device. For example, the lumen device 120 may be an endoscope.

The terminal package 118 may be configured to prevent or reduce microbes and/or other contaminants from entering the terminal package 118. This will be referred to maintaining a "sterile barrier." In some embodiments, for example, the terminal package 118 can include a material suitable for allowing flow of a sterilant fluid, such as hydrogen peroxide ($H_2O_2$) and/or peracetic acid (PAA), into the lumen device receiving area 130 of the terminal package 118 and blocking or reducing the flow of contaminants into the interior of the terminal package 118 to maintain the sterile barrier. In the illustrated embodiment, the terminal package 118 includes a plurality of openings or pores 122 for allowing flow of the sterilant fluid 132 into the terminal package 118. In some embodiments, the pores 122 may be sized so as to allow the sterilant fluid 132 and/or air to communicate into and out of the container 118 as well as prevent microbes from entering the terminal package 118. In the embodiment shown, the multistage connector assembly 127 is integrated into a wall of the terminal package 118 to allow fluid flow out of the terminal package 118. When the terminal package 118 is disconnected after the decontamination process, the multistage connector assembly 127 mechanically maintains the sterile barrier.

The amount of sterilant fluid 132 introduced into the decontamination chamber 104, the lumen device 120 or a combination thereof can be controlled by the system controller 106 by controlling the amount of the sterilant fluid 132 fed or delivered to vaporizer 112. The rate and amount of the sterilant fluid 132 delivered to vaporizer 112 may be preprogrammed into the system controller 106 or may be manually entered into the system controller 106 by a user of the system 100.

To decontaminate a lumen device 120, such as a medical, dental or other device, the lumen device 120 may be sealed within the terminal package 118 and placed in the decontamination chamber 104. The lumen device 120 is then subjected to a decontamination process which may include one or more decontamination cycles. A suitable cycle may include adjusting the pressure of the decontamination chamber 104 to a suitable range, such as to a pressure less than 10 Torr, conditioning using plasma, and introducing the sterilant fluid 132 into the decontamination chamber 104 via vaporizer 112 and nozzle 134. The sterilant fluid may be drawn into the distal end 123 and out the distal end 125 of the lumen device 120. The sterilant fluid 132 may be held within the decontamination chamber 104 for a period of time to facilitate the decontamination of the lumen device 120, and in particular, the exterior surfaces of the lumen device 120. Similarly, the sterilant fluid 132 may be held within the lumen device 120 for a period of time to facilitate the decontamination of the interior surfaces or lumen(s) of the lumen device 120. When the sterilant fluid 132 has been held in the decontamination chamber 104 for the desired or programmed amount of time, the system controller 106 can vent the decontamination chamber 104 to a higher, but sub-atmospheric pressure. The system controller 106 can then hold the pressure within the decontamination chamber 104 for a period of time to further facilitate the decontamination of the load. Following the hold period, the system controller 106 may evacuate the decontamination chamber 104 to remove the sterilant fluid residuals from the decontamination chamber 104 which may also include a plasma treatment to further enhance the removal of the substance residuals, followed by venting the decontamination chamber 104. This cycle or steps may be repeated or extended as part of a comprehensive cycle. When the decontamination cycle ends, the terminal package 118 may be disconnected. The multi-stage connector assembly 127 maintains the sterile barrier of the terminal package 118 upon disconnection.

Figure 3:
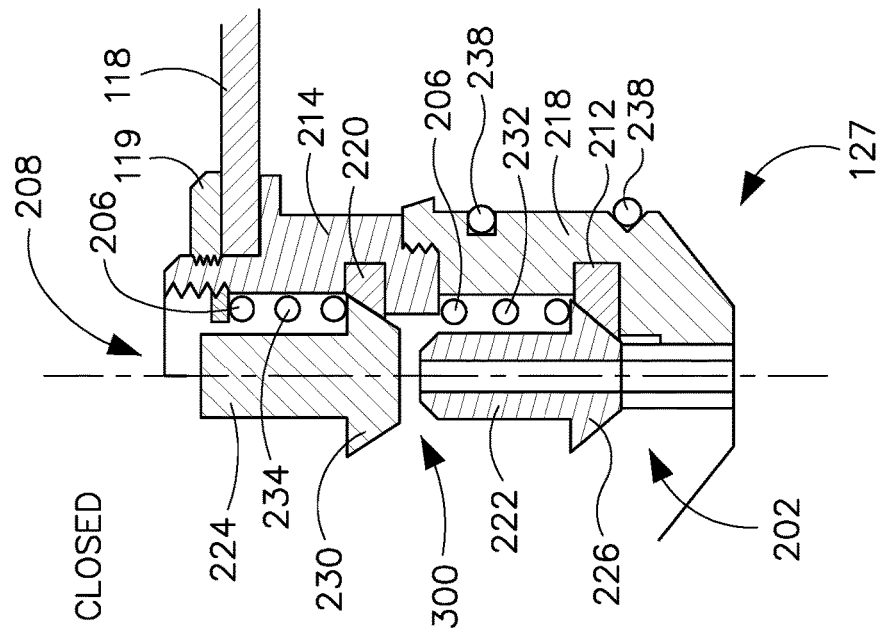
FIG. 3 is a side cross-sectional view of the example multistage connector assembly shown in FIG. 2 in a fully closed position.
Figure 2:
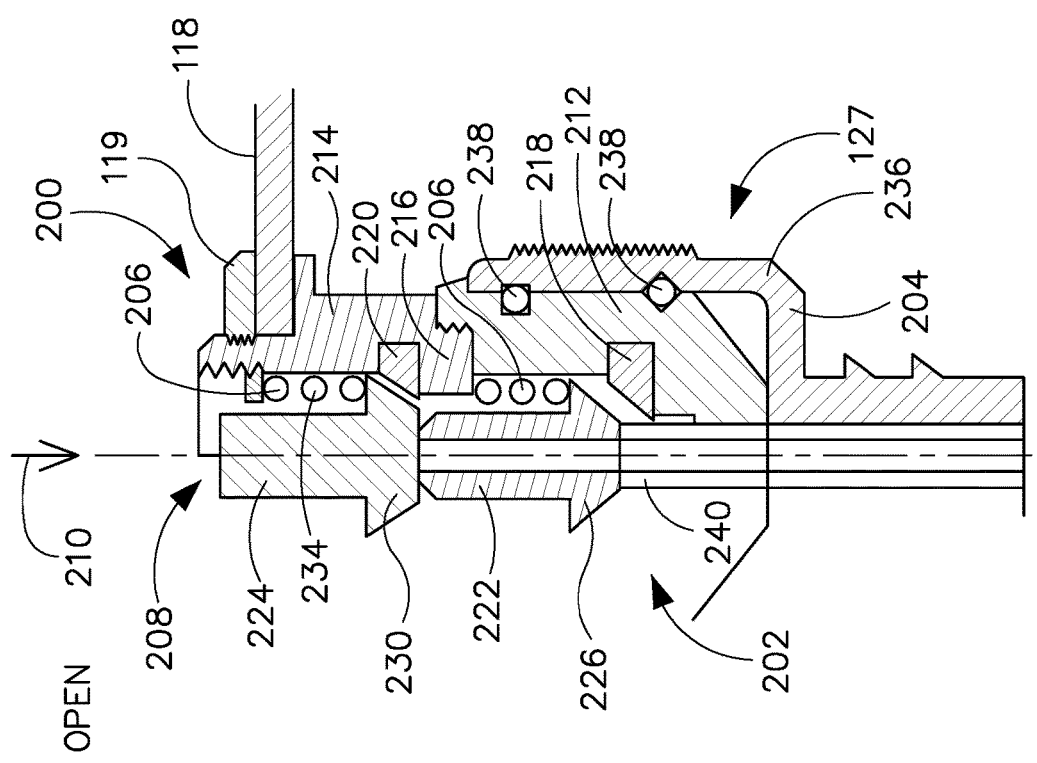
FIG. 2 is a side cross-sectional view of an example multistage connector assembly in a fully open position according to an embodiment of the present disclosure.

FIGS. 2 and 3 are partial side cross-sectional views of the multistage connector assembly 127 in the open and closed positions, respectively, according to an embodiment of this disclosure. In the embodiment shown, the multistage connector assembly 127 includes a main body 200, a multistage barrier 202, a connector 204 and one or more biasing members 206. The multistage barrier 202 is movable in a fluid passageway 208 between a fully closed position (FIG. 3) in which each stage of the multistage barrier 202 is in a closed position in which each stage independently blocks flow in the fluid passageway and a fully open position (FIG. 2) in which each stage is in an open position to allow flow within the fluid passageway. The connector 204 is configured to engage the multistage barrier 202 when coupled to the main body 200 to sequentially open each stage of the multistage barrier 202 to enable fluid communication between the connector 204 and the interior of the terminal package 118.

As shown, the main body defines a fluid passageway 208 to establish fluid communication with the interior of the terminal package 118. In the embodiment shown, the main body is connected with the terminal package 118 with a retaining ring 119. Typically, fluid flow through the fluid passageway 208 is in direction of arrow 210 to draw steriliant fluid out the proximal end 125 of the lumen device 120. The main body 200 includes a plurality of body segments connected together. Although the embodiment shown includes a first body segment 212 connected with a second body segment 214, additional body segments could be provided depending on the circumstances. As shown, the first body segment 212 and the second body segment 214 are threaded together with a threaded connection 216; however, segments 212, 214 could be connected together with an interference fit, a frictional fit, a fastener, an adhesive or other connection manner.

In the embodiment shown, each body segment 212, 214 includes a stage of the multistage barrier 202. Accordingly, by adding additional segments, additional stages could be added to the multistage barrier 202. In the embodiment shown, a first seal 218 is formed in the first body segment 212 and a second seal 220 is formed in the second body segment 214. A first shuttle 222 within the first body segment 212 engages the first seal 218 in the closed position (FIG. 3) to prevent flow through the fluid passageway 208 within the first body segment 212. A second shuttle 224 within the second body segment 214 engages the second seal 220 in the closed position (FIG. 3) to prevent flow through the fluid passageway 208 within the second body segment 214.

As shown, the first shuttle 222 includes a first end with a frustoconical head portion 226 that engages the first seal 218 to prevent fluid flow and a second end that engages a head portion 230 of the second shuttle 224. In the embodiment shown, the head portion 230 of the second shuttle 224 has a frustoconical shape to engage with the second seal 220 to prevent fluid flow. As shown, the biasing members 206, which could be springs, urge the first shuttle 222 and the second shuttle 224 towards their closed positions (FIG. 3). As shown, a first biasing member 232 urges the first shuttle 222 towards the first seal 218 and a second biasing member 234 urges the second shuttle 224 towards the second seal 220.

The connector 204 is configured to be coupled with the main body 200. As shown, the connector 204 includes a shoulder portion 236 that is dimensioned to be received by the first segment 212 of the main body 200. In the embodiment shown, the external surface of the first segment 212 includes grooves to receive seals 238. Although two seals 238 are shown for purposes of example, one or more seals 238 could be provided depending on the circumstances. This creates a sealed connection between the connector 204 and the first segment 212. Embodiments are contemplated in which connector 204 could be coupled with the first segment 212 with a linear motion, a twist motion or other motion. In some cases, the connector 204 and/or first segment 212 could include a user feedback feature in which the user could receive a visual and/or audible feedback (e.g., click) when the connector 204 is fully seated on the first segment 212. In some embodiments, this sealed connection between the connector 204 and one or more seals 238 is established prior to engagement by the connector 204 with the first shuttle 222. This allows the sealed connection to be established before opening the first shuttle 222. Likewise, the seal between the connector 204 and seals 238 continues after the first shuttle 222 closes when the connector 204 is disconnected. This helps maintain a sterile barrier as the connector 204 is disconnected.

In the embodiment shown, the connector 204 includes a tip 240 that engages a portion of the multistage barrier 202 when the connector 204 is coupled with the main body 200 to move at least one stage of the multistage barrier from a closed position to an open position. As shown, the tip 240 engages the first shuttle 222 to move the first shuttle 222 from the closed position (FIG. 3) to the open position (FIG. 2). In some cases, the tip 240 extends into the fluid passageway 208 when the connector 204 is coupled with the main body 200. In some embodiments, the tip 204 is dimensioned to engage the first shuttle 222 after the connector 204 makes a sealed connection with at least one seal 238. This allows the sealed connection between the connector 204 and one or more seals 238 to be established before opening of the first shuttle 222 by the tip 240. Likewise, this allows the sealed connection to continue after closing of the first shuttle 222.

In the closed position shown in FIG. 3, there is a spaced apart area 300 between the first shuttle 222 and the second shuttle 224. This spacing allows the shuttles 222, 224 to be engaged sequentially (i.e., independently opened/closed). In the embodiment shown, as the connector 204 is coupled with the main body 200, the connector 204 establishes a sealed connection with one or more seals 238. The tip 240 then engages the head portion 226 of the first shuttle 222. This force overcomes the first biasing member 232 to move the head portion 226 of the first shuttle 222 away from the first seal 218, which opens that stage of the multistage barrier 202. Due to the spaced apart area 300, the first shuttle 222 can move a distance before engaging the second shuttle 224. Accordingly, in the initial movement of the tip 240, the first segment 222 is open, but the second segment 224 remains closed. As the tip 240 continues to move towards the first segment 222 (as the connector 204 is being coupled with the main body 200), the first segment 222 engages the second segment 224. This movement overcomes the second biasing member 234 to move the head portion 230 of the second shuttle 224 away from the second seal 220, which opens the second segment 224. Thus, with the connector 204 fully seated, both segments 222, 224 are open to allow fluid communication with the interior of the terminal package 118.

After a decontamination process, the connector 204 can be disconnected from the main body 200. As the connector 204 disconnects, the stages sequentially close until all stages are closed when the connector 204 is fully disconnected. In the embodiment shown, as the connector 204 is being disconnected, the second shuttle 224 closes, and then the first shuttle 222, and then the sealed connection between the connector 204 becomes disconnected. In this manner, the multistage connector assembly 127 mechanically maintains the terminal package's sterile barrier when the connector 204 is disconnected.

EXAMPLES

Illustrative examples of the method and system disclosed herein are provided below. An embodiment of the method and system may include any one or more, and any combination of, the examples described below.

Example 1 is a decontamination system for a lumen device. The decontamination system comprises a decontamination chamber, a terminal package, and a connector assembly. The decontamination chamber defines a lumen device receiving area. The terminal package is dimensioned to be received within the lumen device receiving area and is configured to establish a sterile barrier for an interior of the terminal package. The connector assembly is operably associated with the terminal package. The connector assembly comprises a main body, a multistage barrier, a connector, and one or more biasing members. The main body defines a fluid passageway to establish fluid communication with the interior of the terminal package. The multistage barrier is movable in the fluid passageway between a fully closed position in which each stage of the multistage barrier is in a closed position in which each stage independently blocks flow in the fluid passageway and a fully open position in which each stage is in an open position to allow flow within the fluid passageway. The connector is configured to be coupled with the main body such that the connector engages the multistage barrier when coupled to the main body to sequentially open each stage of the multistage barrier to enable fluid communication between the connector and the interior of the terminal package. The biasing member(s) are configured to urge each stage of the multistage barrier towards a closed position that blocks flow in the fluid passageway.

In Example 2, the subject matter of Example 1 is further configured such that the multistage barrier is configured to move to a partially closed position between the fully closed and fully open positions such that in the partially closed position, one or more stages of the multistage barrier are in the closed position and one or more stages are in the open position.

In Example 3, the subject matter of Example 1 is further configured such that the multistage barrier includes a first barrier engageable by the connector when the connector is coupled with the main body such that the first barrier is movable from a closed position in which the first barrier prevents flow in the fluid passageway to an open position in which the first barrier allows flow in the fluid passageway upon engagement by the connector.

In Example 4, the subject matter of Example 3 is further configured such that the multistage barrier further comprises a second barrier engageable by the first barrier to move the second barrier from a closed position in which the second barrier prevents flow in the fluid passageway to an open position in which the second barrier allows flow in the fluid passageway.

In Example 5, the subject matter of Example 4 is further configured such that the first barrier and the second barrier are spaced-apart in their respective closed positions.

In Example 6, the subject matter of Example 4 is further configured such that the first barrier is movable between a first position and a second position, wherein a second stage engagement point is positioned between the first position and the second position, wherein the first barrier travels independently between the first position and the second stage engagement point, and wherein the first barrier engages the second barrier between the second stage engagement point and the second position so the first barrier and the second barrier travel in unison between the second stage engagement point and the second position.

In Example 7, the subject matter of Example 1 is further configured such that the main body comprises a plurality of body segments connected together.

In Example 8, the subject matter of Example 7 is further configured such that each body segment of the plurality of body segments includes a stage of the multistage barrier.

In Example 9, the subject matter of Example 8 is further configured such that each segment includes a seal engageable by a respective stage of the multistage barrier to block fluid flow within that respective body segment.

In Example 10, the subject matter of Example 9 is further configured such that each segment includes a biasing member to move the respective stage within the body segment towards a closed position that blocks flow within that respective body segment.

In Example 11, the subject matter of Example 10 is further configured such that each body segment includes a shoulder to retain the biasing member with that respective body segment.

In Example 12, the subject matter of Example 1 is further configured such that the main body is integral with the terminal package.

In Example 13, the subject matter of Example 1 is further configured such that the connector includes a tip that engages a portion of the multistage barrier when the connector is coupled with the main body to move at least one stage of the multistage barrier from a closed position to an open position.

In Example 14, the subject matter of Example 13 is further configured such that the tip extends into the fluid passageway when the connector is coupled with the main body.

In Example 15, the subject matter of Example 1 is further configured such that the multistage barrier comprises a plurality of shuttles movable within the fluid passageway, wherein each shuttle is configured to independently block flow in the fluid passageway.

In Example 16, the subject matter of Example 15 is further configured such that the plurality of shuttles are longitudinally spaced apart in their respective closed positions.

In Example 17, the subject matter of Example 16 is further configured such that the shuttles are arranged to be sequentially movable to an open position as the connector couples with the main body.

Example 18 is a multistage connector assembly with a main body, a multistage body, a multistage barrier, a connector, and one or more biasing members. The main body defines a fluid passageway therethrough. The assembly includes a multistage barrier movable in the fluid passageway between a fully closed position in which each stage of the multistage barrier is in a closed position to each independently block flow in the fluid passageway and a fully open position in which each stage is in an open position to allow flow within the fluid passageway. The connector is configured to be coupled with the main body. The connector is configured to engage the multistage barrier when coupled to the main body to sequentially open each stage of the multistage barrier to enable flow through the fluid passageway. The one or more biasing members are configured to urge each stage of the multistage barrier towards a closed position that blocks flow in the fluid passageway.

In Example 19, the subject matter of Example 18 is further configured such that the multistage barrier comprises a plurality of spaced-part shuttles movable within the fluid passageway, wherein each shuttle is configured to independently block flow in the fluid passageway in a closed position.

In Example 20, the subject matter of Example 19 is further configured such that the plurality of shuttles are arranged to be sequentially movable to an open position as the connector couples with the main body to enable flow through the fluid passageway.

Although the present disclosure has been described with reference to particular means, materials and embodiments, from the foregoing description, one skilled in the art can easily ascertain the essential characteristics of the invention and various changes and modifications may be made to adapt the various uses and characteristics without departing from the spirit and scope of the invention.

What is claimed is:

1. A decontamination system for a lumen device, the decontamination system comprising:
   (i) a decontamination chamber defining a lumen device receiving area;
   (ii) a terminal package dimensioned to be received within the lumen device receiving area, wherein the terminal package is configured to establish a sterile barrier for an interior of the terminal package; and
   (iii) a connector assembly operably associated with the terminal package, wherein the connector assembly comprises:
      (a) a main body defining a fluid passageway to establish fluid communication with the interior of the terminal package;
      (b) a multistage barrier movable in the fluid passageway between a fully closed position in which each stage of the multistage barrier is in a closed position in which each stage independently blocks flow in the fluid passageway and a fully open position in which each stage is in an open position to allow flow within the fluid passageway;
      (c) a connector configured to be coupled with the main body, wherein the connector is configured to engage the multistage barrier when coupled to the main body to sequentially open each stage of the multistage barrier to enable fluid communication between the connector and the interior of the terminal package; and
      (d) one or more biasing members configured to urge each stage of the multistage barrier towards a closed position that blocks flow in the fluid passageway.

2. The decontamination system of claim 1, wherein the multistage barrier is configured to move to a partially closed position between the fully closed and fully open positions, wherein in the partially closed position, one or more stages of the multistage barrier are in the closed position and one or more stages are in the open position.

3. The decontamination system of claim 1, wherein the multistage barrier includes a first barrier engageable by the connector when the connector is coupled with the main body, wherein the first barrier is movable from a closed position in which the first barrier prevents flow in the fluid passageway to an open position in which the first barrier allows flow in the fluid passageway upon engagement by the connector.

4. The decontamination system of claim 3, wherein the multistage barrier further comprises a second barrier engageable by the first barrier to move the second barrier from a closed position in which the second barrier prevents flow in the fluid passageway to an open position in which the second barrier allows flow in the fluid passageway.

5. The decontamination system of claim 4, wherein the first barrier and the second barrier are spaced-apart in their respective closed positions.

6. The decontamination system of claim 4, wherein the first barrier is movable between a first position and a second position, wherein a second stage engagement point is positioned between the first position and the second position, wherein the first barrier travels independently between the first position and the second stage engagement point, and wherein the first barrier engages the second barrier between the second stage engagement point and the second position so the first barrier and the second barrier travel in unison between the second stage engagement point and the second position.

7. The decontamination system of claim 1, wherein the main body comprises a plurality of body segments connected together.

8. The decontamination system of claim 7, wherein each body segment of the plurality of body segments includes a stage of the multistage barrier.

9. The decontamination system of claim 8, wherein each segment includes a seal engageable by a respective stage of the multistage barrier to block fluid flow within that respective body segment.

10. The decontamination system of claim 9, wherein each segment includes a biasing member to move the respective stage within the body segment towards a closed position that blocks flow within that respective body segment.

11. The decontamination system of claim 10, wherein each body segment includes a shoulder to retain the biasing member with that respective body segment.

12. The decontamination system of claim 1, wherein the main body is integral with the terminal package.

13. The decontamination system of claim 1, wherein the connector includes a tip that engages a portion of the multistage barrier when the connector is coupled with the main body to move at least one stage of the multistage barrier from a closed position to an open position.

14. The decontamination system of claim 13, wherein the tip extends into the fluid passageway when the connector is coupled with the main body.

15. The decontamination system of claim 1, wherein the multistage barrier comprises a plurality of shuttles movable within the fluid passageway, wherein each shuttle is configured to independently block flow in the fluid passageway.

16. The decontamination system of claim 15, wherein the plurality of shuttles are longitudinally spaced apart in their respective closed positions.

17. The decontamination system of claim 16, wherein the shuttles are arranged to be sequentially movable to an open position as the connector couples with the main body.

18. A multistage connector assembly comprising:
   a main body defining a fluid passageway therethrough;
   a multistage barrier movable in the fluid passageway between a fully closed position in which each stage of the multistage barrier is in a closed position to each independently block flow in the fluid passageway and a fully open position in which each stage is in an open position to allow flow within the fluid passageway;
   a connector configured to be coupled with the main body, wherein the connector is configured to engage the multistage barrier when coupled to the main body to sequentially open each stage of the multistage barrier to enable flow through the fluid passageway; and
   one or more biasing members configured to urge each stage of the multistage barrier towards a closed position that blocks flow in the fluid passageway.

19. The multistage connector assembly of claim 18, wherein the multistage barrier comprises a plurality of spaced-part shuttles movable within the fluid passageway, wherein each shuttle is configured to independently block flow in the fluid passageway in a closed position.

20. The multistage connector assembly of claim 19, wherein the plurality of shuttles are arranged to be sequentially movable to an open position as the connector couples with the main body to enable flow through the fluid passageway.

\* \* \* \* \*